United States Patent
Kutzik et al.

(10) Patent No.: US 10,959,845 B2
(45) Date of Patent: Mar. 30, 2021

(54) ADJUSTABLE ANNULOPLASTY DEVICE WITH ALTERNATING PEAKS AND TROUGHS

(71) Applicant: Valtech Cardio, Ltd., Or Yehuda (IL)

(72) Inventors: Meir Kutzik, Holon (IL); Haim Brauon, Beit Dagan (IL); Michael Levin, Carmi Yosef (IL); Alon Fogel, Tel Aviv-Jaffa (IL); Ilia Hariton, Zichron Yaacov (IL); Tal Reich, Moledet (IL)

(73) Assignee: Valtech Cardio, Ltd., Or Yehuda (IL)

( * ) Notice: Subject to any disclaimer, the term of this patent is extended or adjusted under 35 U.S.C. 154(b) by 0 days.

(21) Appl. No.: 16/261,975

(22) Filed: Jan. 30, 2019

(65) Prior Publication Data
US 2019/0159898 A1   May 30, 2019

Related U.S. Application Data

(63) Continuation of application No. 15/475,871, filed on Mar. 31, 2017, now Pat. No. 10,226,342.

(30) Foreign Application Priority Data

Jul. 8, 2016  (GB) ...................................... 1611910

(51) Int. Cl.
    *A61F 2/24*    (2006.01)
(52) U.S. Cl.
    CPC .... *A61F 2/2445* (2013.01); *A61F 2220/0016* (2013.01); *A61F 2220/0091* (2013.01);
    (Continued)
(58) Field of Classification Search
    CPC .............................................. A61F 2220/0091
    See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| EP | 1034753 A1 | 9/2000 |
| EP | 3531975 A1 | 9/2019 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Jacqueline Woznicki
(74) *Attorney, Agent, or Firm* — Thomas C. Richardson

(57) ABSTRACT

An implant that includes a ring, anchors, and adjustment elements is advanced to a subject's heart valve. The ring includes hinges, and struts arranged in a pattern of alternating peaks and troughs. The ring circumscribes a central axis. At least one hinge is disposed at each trough. Each strut has a first end-portion and a second end-portion. Each peak is defined by convergence of adjacent first end-portions. Each trough is defined by convergence of adjacent second end-portions. Each anchor has a longitudinal axis. Within the heart, the longitudinal axis of at least one of the anchors is deflected with respect to the central axis, and each of the anchors is driven along its longitudinal axis with respect to the trough and into tissue of the heart. Subsequently, tissue of the heart is contracted by rotating the plurality of adjustment elements. Other embodiments are also described.

13 Claims, 11 Drawing Sheets

(52) U.S. Cl.
CPC .............. *A61F 2250/0006* (2013.01); *A61F 2250/0008* (2013.01); *A61F 2250/0012* (2013.01); *A61F 2250/0029* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,801,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,113,612 A * | 9/2000 | Swanson .............. A61F 2/88 623/1.15 |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,585,755 B2 | 7/2003 | Jackson et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |

(56) References Cited

U.S. PATENT DOCUMENTS

| | | |
|---|---|---|
| 6,770,083 B2 | 8/2004 | Seguin |
| 6,786,924 B2 | 9/2004 | Ryan et al. |
| 6,786,925 B1 | 9/2004 | Shoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |

(56) References Cited

U.S. PATENT DOCUMENTS

| | | | |
|---|---|---|---|
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,591,576 B2 | 11/2013 | Hasenkam et al. |
| 8,608,797 B2 | 12/2013 | Gross et al. |
| 8,628,569 B2 | 1/2014 | Benichou |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,645,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 * | 11/2015 | Lashinski ................ A61F 2/02 |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0220683 A1 * | 11/2003 | Minasian ................ A61F 2/82 623/1.15 |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |

(56) References Cited

U.S. PATENT DOCUMENTS

| | | |
|---|---|---|
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1* | 3/2005 | Lashinski ............. A61F 2/2466 623/2.37 |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0240259 A1* | 10/2005 | Sisken ..................... A61F 2/02 623/1.36 |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161244 A1* | 7/2006 | Seguin ..................... A61F 2/07 623/1.23 |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |

(56) References Cited

U.S. PATENT DOCUMENTS

| | | |
|---|---|---|
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0022557 A1* | 1/2012 | Cabiri ............... A61B 17/064 606/139 |
| 2012/0053628 A1 | 3/2012 | Sojka et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2012/0330411 A1* | 12/2012 | Gross ............... A61F 2/2466 623/2.37 |
| 2013/0030522 A1 | 1/2013 | Rowe et al. |
| 2013/0046373 A1* | 2/2013 | Cartledge ............. A61F 2/243 623/1.11 |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |

(56) References Cited

U.S. PATENT DOCUMENTS

| | | |
|---|---|---|
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243659 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0135506 A1* | 5/2015 | White .................. A61F 2/2415 29/428 |
| 2015/0230919 A1 | 6/2015 | Chau et al. |
| 2015/0182336 A1 | 7/2015 | Zipory et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0168603 A1 | 6/2016 | Garg et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2018/0008409 A1* | 1/2018 | Kutzik .................. A61F 2/2445 |
| 2018/0049875 A1 | 2/2018 | Iflah et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |

OTHER PUBLICATIONS

Ahrnadi, A., G. Spillner, and Th Johannesson. "Hemodynamic changes following experimental production and correction of acute mitral regurgitation with an adjustable ring prosthesis," The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Sung. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriforrn Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success- midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

(56) References Cited

OTHER PUBLICATIONS

O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence, Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

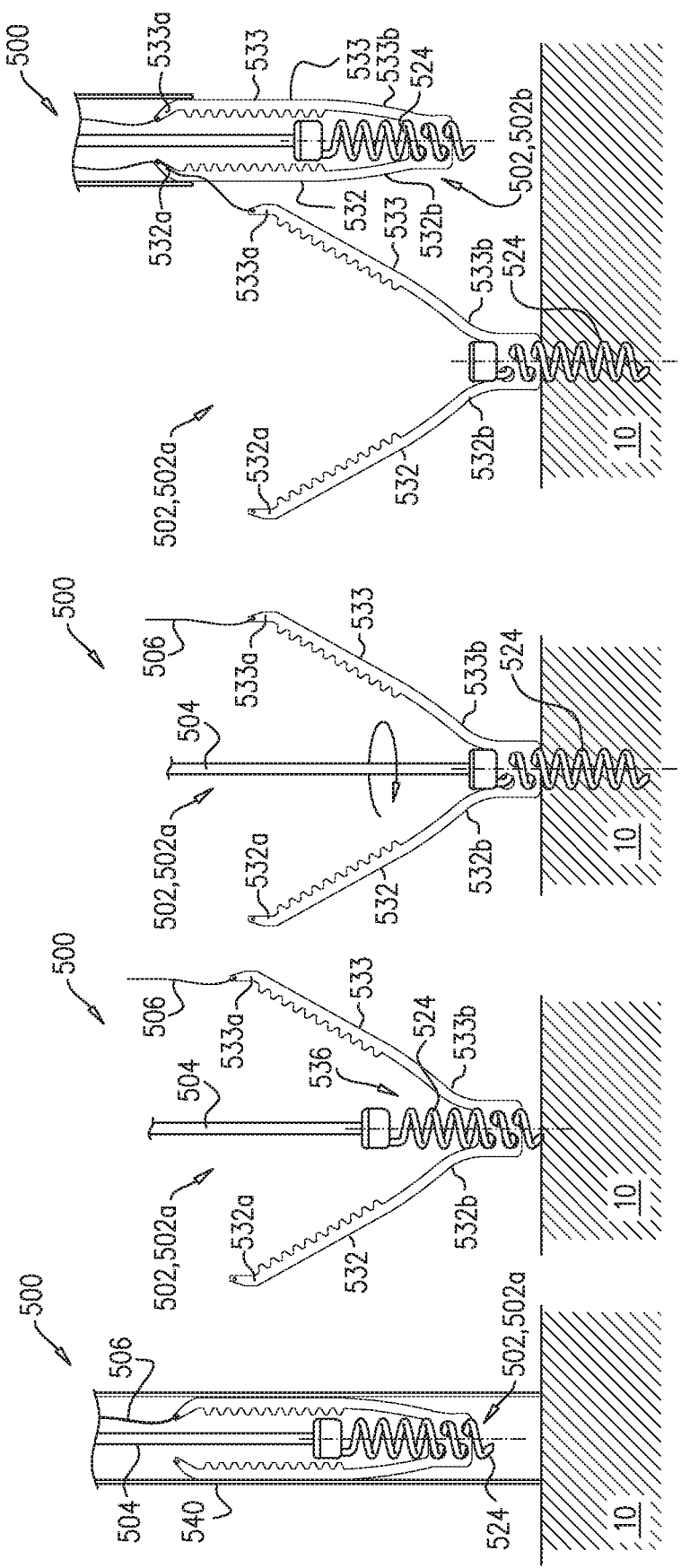

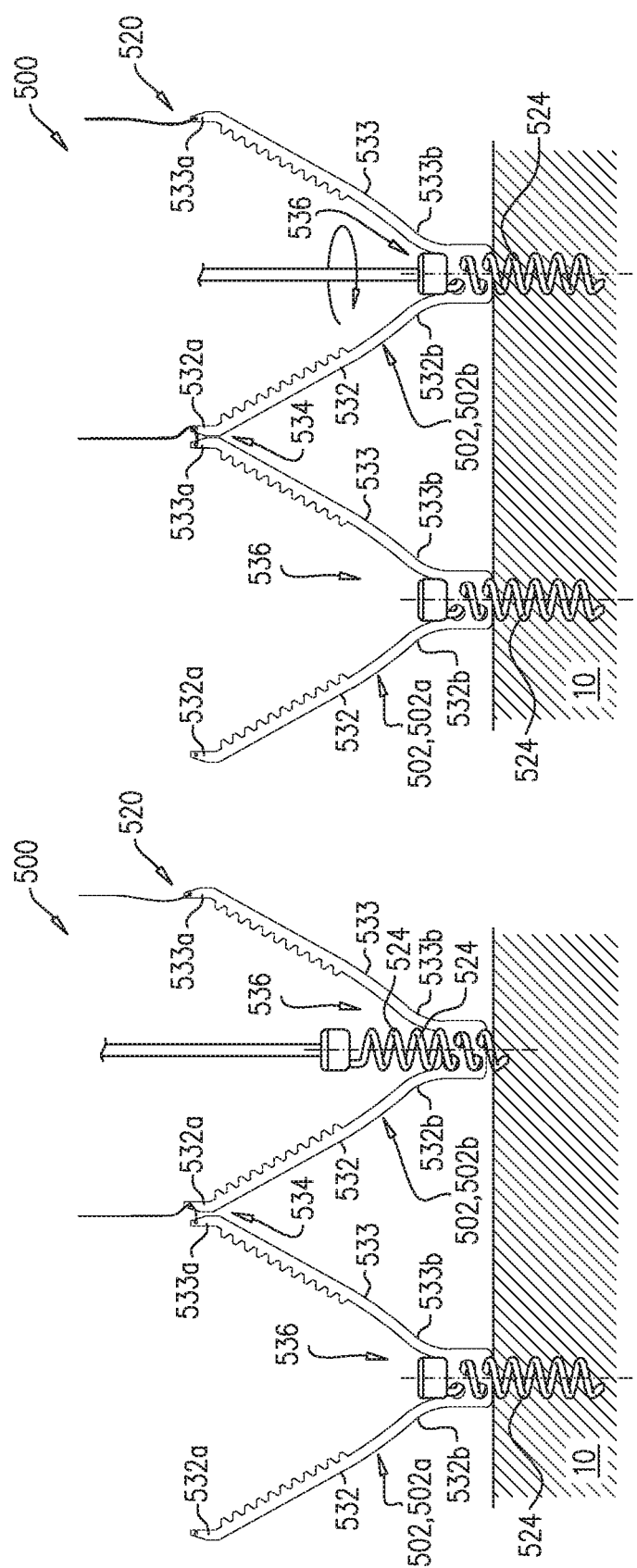

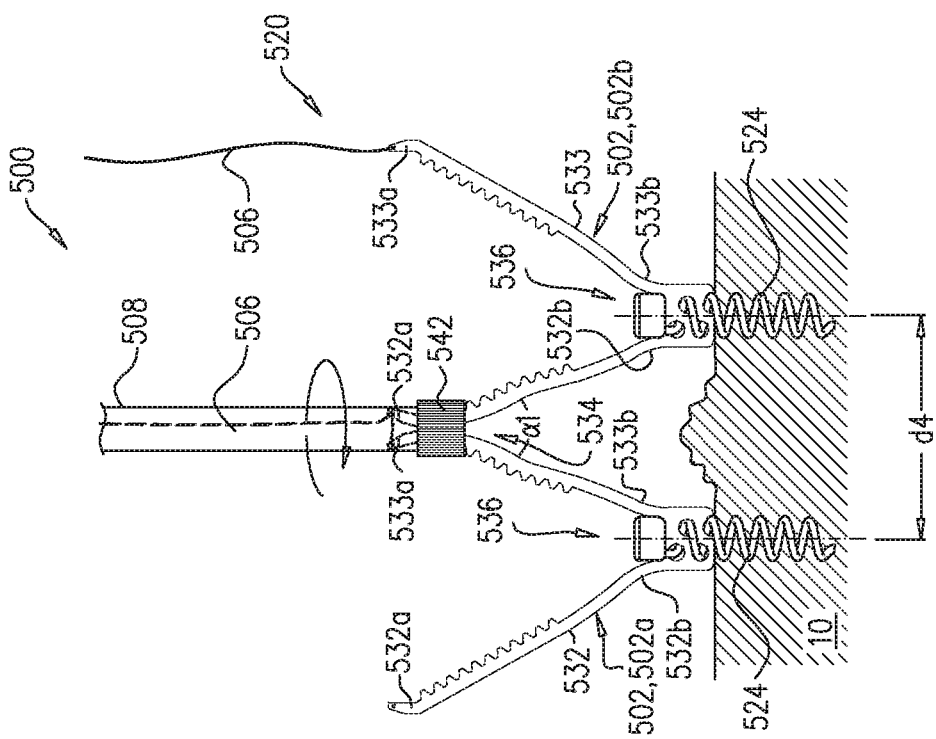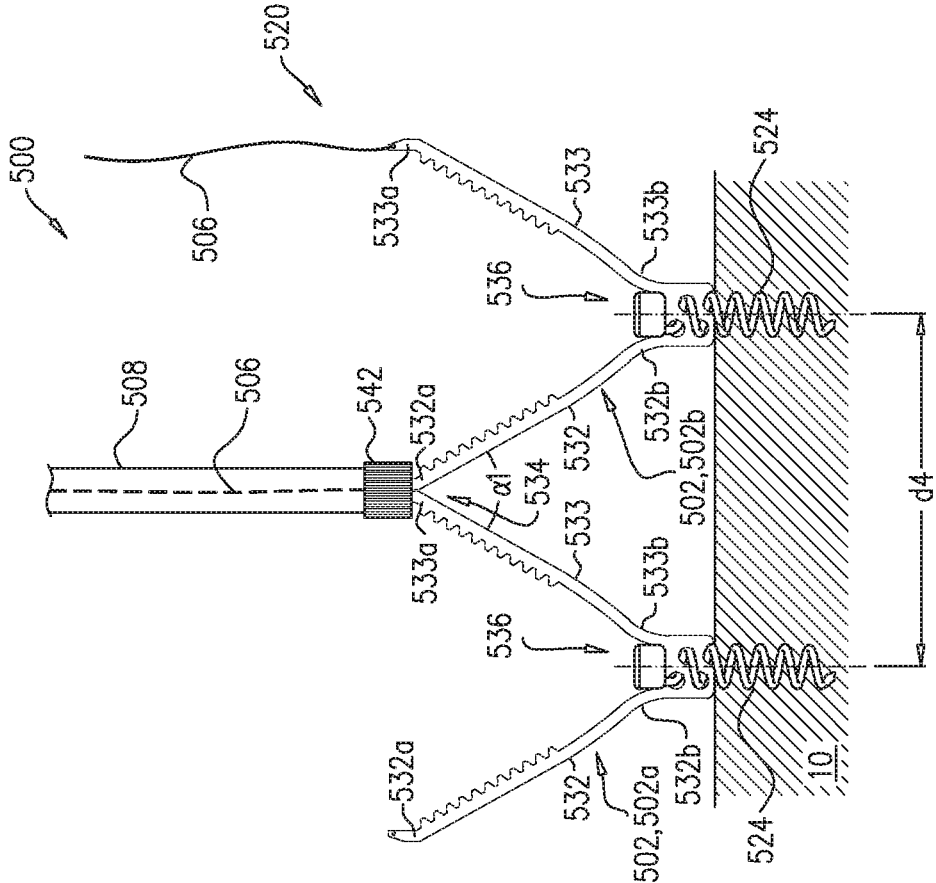

ADJUSTABLE ANNULOPLASTY DEVICE WITH ALTERNATING PEAKS AND TROUGHS

CROSS-REFERENCE TO RELATED APPLICATIONS

The present application is a Continuation of U.S. Ser. No. 15/475,871 to Kutzik et al., filed Mar. 31, 2017, and entitled "Adjustable annuloplasty device with alternating peaks and troughs," which published as US 2018/0008409, and which claims priority from UK Patent Application GB1611910.9, filed Jul. 8, 2016, and entitled "Adjustable annuloplasty device with alternating peaks and troughs," which is incorporated herein by reference.

FIELD OF THE INVENTION

The present invention relates in general to valve repair. More specifically, the present invention relates to repair of a cardiac valve of a patient using an adjustable implant.

BACKGROUND

Dilation of the annulus of atrioventricular heart valves, such as the mitral valve, prevents the valve leaflets from coapting effectively when the valve is closed, thereby resulting in regurgitation of blood from the ventricle through the valve into the atrium. Annuloplasty is a known surgical technique for treatment of a dilated valve annulus. U.S. Pat. No. 9,180,005 to Lashinski et al., which is incorporated herein by reference, relates to an adjustable mitral valve ring for minimally-invasive delivery.

SUMMARY OF THE INVENTION

Annuloplasty implants are described, which are configured to be percutaneously (e.g., transluminally) delivered to the heart, and adjusted in order to reshape the valve annulus. The anchors comprise a ring and tissue anchors for anchoring the ring to the valve annulus. For some applications, the implants facilitate deflection or pivoting of the tissue anchors with respect to the ring. For some applications, the implants comprise a plurality of subunits that are individually advanceable and anchorable to the valve annulus. Once at the valve, the subunits are connected to form a ring, and the ring is adjusted to reshape the valve annulus.

There is therefore provided, in accordance with an application of the present invention, apparatus for use at a valve of a heart of a subject, the apparatus including:
  a ring, including a plurality of struts arranged in a pattern of alternating peaks and troughs,
    each strut having a first end-portion and a second end-portion,
    each peak defined by convergence of adjacent first end-portions disposed at an angle with respect to each other, and
    each trough defined by convergence of adjacent second end-portions; and
  a plurality of anchors, each anchor:
    having a longitudinal axis,
    configured to be driven along the longitudinal axis into tissue of the heart,
    coupled to the ring at a respective trough in a manner that facilitates:
      movement of the anchor along the longitudinal axis with respect to the trough, and
      deflection of the longitudinal axis with respect to the trough.

In an application, the apparatus further includes at least one anchor driver, couplable to the plurality of anchors, and configured to anchor the ring to the heart by moving each anchor along its longitudinal axis with respect to its respective trough.

In an application:
  the ring further includes a plurality of adjustment elements, and
  each adjustment element is movably coupled to respective adjacent first end-portions such that movement of the adjustment element with respect to the adjacent first end-portions changes the angle at which the adjacent first end-portions are disposed with respect to each other.

In an application, the apparatus further includes at least one adjustment tool, reversibly couplable to the plurality of adjustment elements, and configured to move each adjustment element with respect to its respective adjacent first end-portions.

In an application, the adjustment tool is configured to rotate each adjustment element with respect to its respective adjacent first end-portions.

In an application, each adjustment element circumscribes both of the respective adjacent first end-portions.

In an application, the apparatus further includes at least one adjustment tool, reversibly couplable to the plurality of adjustment elements, and configured to rotate each adjustment element around both of its respective adjacent first end-portions.

In an application:
  the ring includes a plurality of hinges,
  at least one hinge of the plurality of hinges is disposed at each trough, and
  at each trough, the respective anchor is coupled to the ring via the at least one hinge.

In an application, each hinge couples the adjacent second end-portions to each other.

In an application, each hinge is a flexure bearing.

In an application, each hinge includes a fabric.

In an application, each anchor is shaped and rotatably coupled to the ring at the respective trough such that rotation of the respective anchor with respect to the ring moves the anchor along its longitudinal axis with respect to the trough.

In an application:
  the ring includes a plurality of anchor mounts,
  at each trough:
    a respective anchor mount of the plurality of anchor mounts is articulatably coupled (i) to one second end-portion via a first hinge of the plurality of hinges, and (ii) to another second end-portion via a second hinge of the plurality of hinges, and
    the respective anchor is rotatably coupled to the respective anchor mount.

In an application, at each trough the respective anchor is rotatably coupled to the respective anchor mount such that rotation of the respective anchor with respect to the respective anchor mount moves the anchor along its longitudinal axis with respect to the anchor mount.

There is further provided, in accordance with an application of the present invention, a method for use with a valve of a heart of a subject, the method composing:
  transfemorally delivering a plurality of subunits to the heart, each of the subunits including a pair of struts that includes a first strut and a second strut, each strut of the pair having a first end-portion and a second end-portion, each of the subunits defining a trough at which the second end-portion of each strut of the pair is coupled to the second end-portion of the other strut of the pair;

for each subunit, anchoring the trough to tissue that surrounds the valve by driving a tissue anchor into the tissue;

securing the first end-portion of the second strut of a first subunit to the first end-portion of the first strut of a second subunit such that the secured first end-portions converge at an angle to define a peak; and subsequently to the steps of anchoring and securing, reducing the angle of each peak by actuating a respective adjustment element.

In an application, transfemorally delivering the plurality of subunits to the heart includes:

transfemorally delivering the first subunit to the heart while a longitudinal guide member is coupled to the first-end portion of the second strut of the first subunit;

transfemorally delivering the second subunit to the heart; and subsequently, guiding the second subunit toward the first subunit by sliding the first end-portion of the first strut of the second subunit over and along the longitudinal guide member to the first-end portion of the second strut of the first subunit.

In an application, the method includes forming a ring from the plurality of subunits.

In an application, actuating the respective adjustment element includes rotating the respective adjustment element with respect to the respective peak.

In an application, the method further includes, subsequently to the step of anchoring, coupling the respective adjustment elements to the first end-portions that define each peak.

In an application, coupling the respective adjustment elements to the first end portions that define each peak includes coupling the respective adjustment elements to the first end portions that define each peak subsequently to securing the step of securing.

The present invention will be more fully understood from the following detailed description of applications thereof, taken together with the drawings, in which:

BRIEF DESCRIPTION OF THE DRAWINGS

FIGS. 9A-J are schematic illustrations of a system that comprises a plurality of subunits that are intracorporeally assembled to form an implant, in accordance with some applications of the invention.

DETAILED DESCRIPTION OF EMBODIMENTS

Figure 1A:
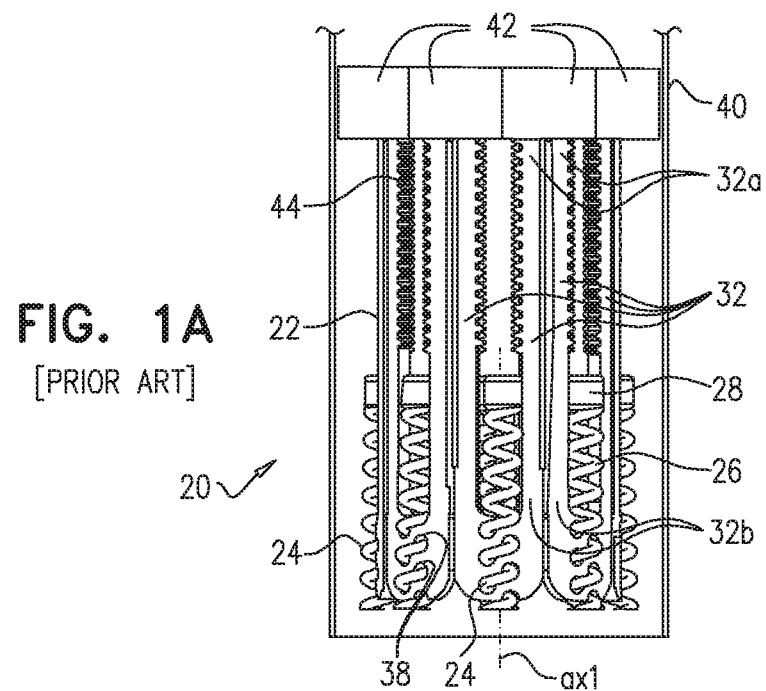
FIGS. 1A-D are schematic illustrations of a prior art implant for use at a valve of a heart of a subject, in accordance with some applications of the invention.

Reference is made to FIGS. 1A-D, which are schematic illustrations of a prior art implant 20 shown in U.S. Pat. No. 9,180,005, for use at a valve (e.g., a mitral valve) of a heart of a subject, in accordance with some applications of the invention. Implant 20 comprises a ring 22 and a plurality of (e.g., 8) anchors 24. Ring 22 comprises a plurality of struts 32 arranged in a pattern of alternating peaks 34 and troughs 36 (e.g., in a zig-zag pattern). Each strut 32 has a first end-portion 32a and a second end-portion 32b. Each peak 34 is defined by convergence of adjacent first end-portions 32a (i.e., of first end-portions 32a of adjacent struts 32), and each trough 36 is defined by convergence of adjacent second end-portions 32b (i.e., of second end-portions 32b of adjacent struts 32).

Each anchor 24 has a longitudinal axis ax1 along which it is configured to be driven into tissue of the annulus of the valve of the heart of the subject, and is coupled to ring 22 at a respective trough 36 in a manner that facilitates movement of the anchor along the longitudinal axis with respect to the trough. At each trough 36, ring 22 defines a plurality of holes 38 through which anchor 24 is moveable. Each anchor 24 comprises a helical tissue-engaging element 26, and an anchor head 28, and is shaped and rotatably coupled to ring 22 at the respective trough 36 such that rotation of the anchor with respect to the ring moves the anchor along its longitudinal axis with respect to the trough (e.g., corkscrews the anchor through holes 38 such that the anchor moves longitudinally). This is illustrated by FIGS. 1B-C, which show anchors 24 in a retracted position (FIG. 1B), and in an extended position after having moved along axis ax1 with respect to its respective trough 36 (FIG. 1C).

Implant 20 comprises an adjustment element 42 for each pair of adjacent first-end portions 32a. Adjustment element 42 is typically an internally-threaded nut that screws onto an external thread 44 (visible in FIG. 1D) defined by the adjacent first-end portions 32a. Such adjustment elements are actuated by rotation (e.g., using an adjustment tool, not shown), and as the adjustment elements are screwed further onto and over struts 32, the angle alpha_1 at which first end-portions 32a converge becomes smaller.

Figure 1B:
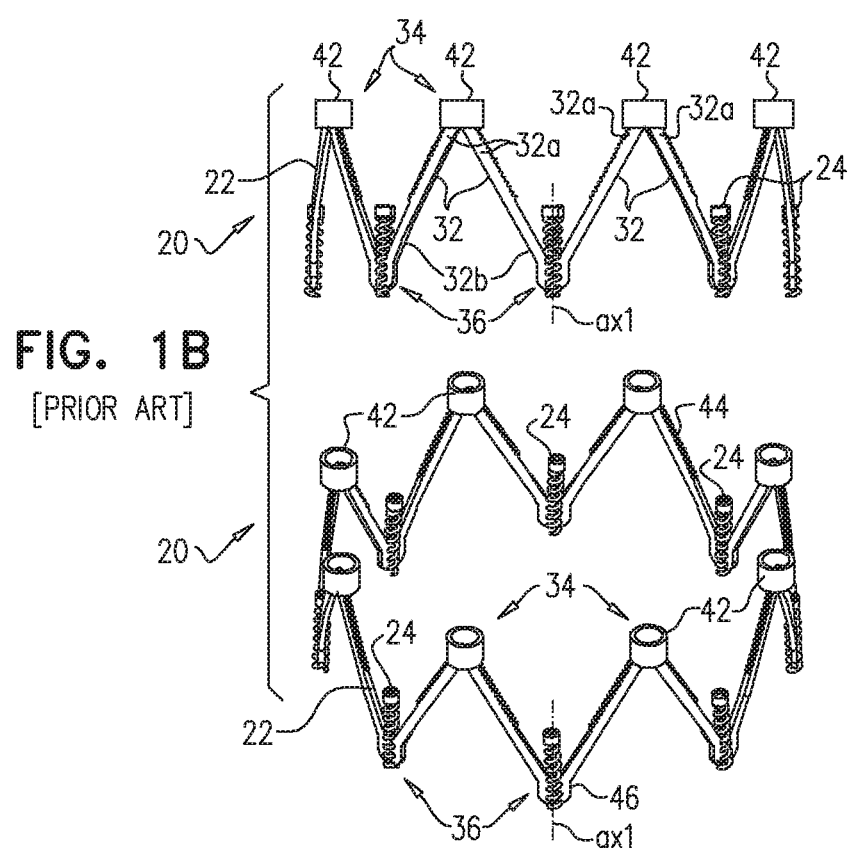
Figure 1C:
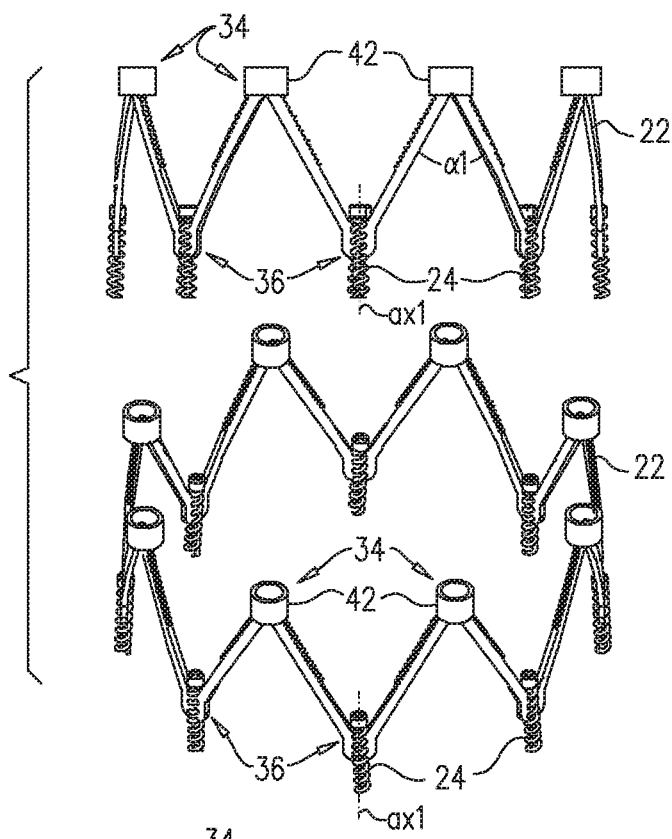
Figure 1D:
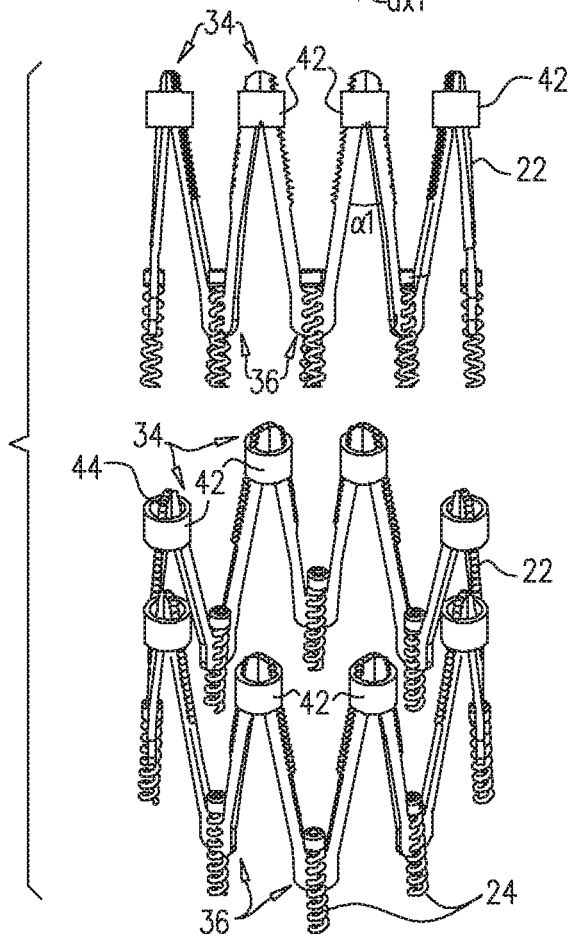

Implant 20 is an annuloplasty device, and is delivered to the heart percutaneously while in a compressed state, via a catheter 40 (FIG. 1A). Within the heart (e.g., within an atrium, such as the left atrium) implant 20 is deployed from the catheter, and automatically expands into an expanded state (FIG. 1B). While in its expanded state, implant 20 is anchored to tissue of the annulus of the valve by driving the anchors along axis ax1 and into the tissue (FIG. 1C). Typically, implant 20 is positioned such that ring 22 surrounds the orifice of the valve. Once implant 20 is anchored, it is contracted by actuating adjustment elements 42, such that angle alpha_1 is reduced (compare FIG. 1C to FIG. 1D). Contraction of implant 20 reduces (i) the circumference and the diameter of ring 22, (ii) the distance between adjacent and opposite anchors 24, and thereby (iii) the circumference and the diameter of the valve of the heart, thereby improving function of the valve.

Figure 2A:
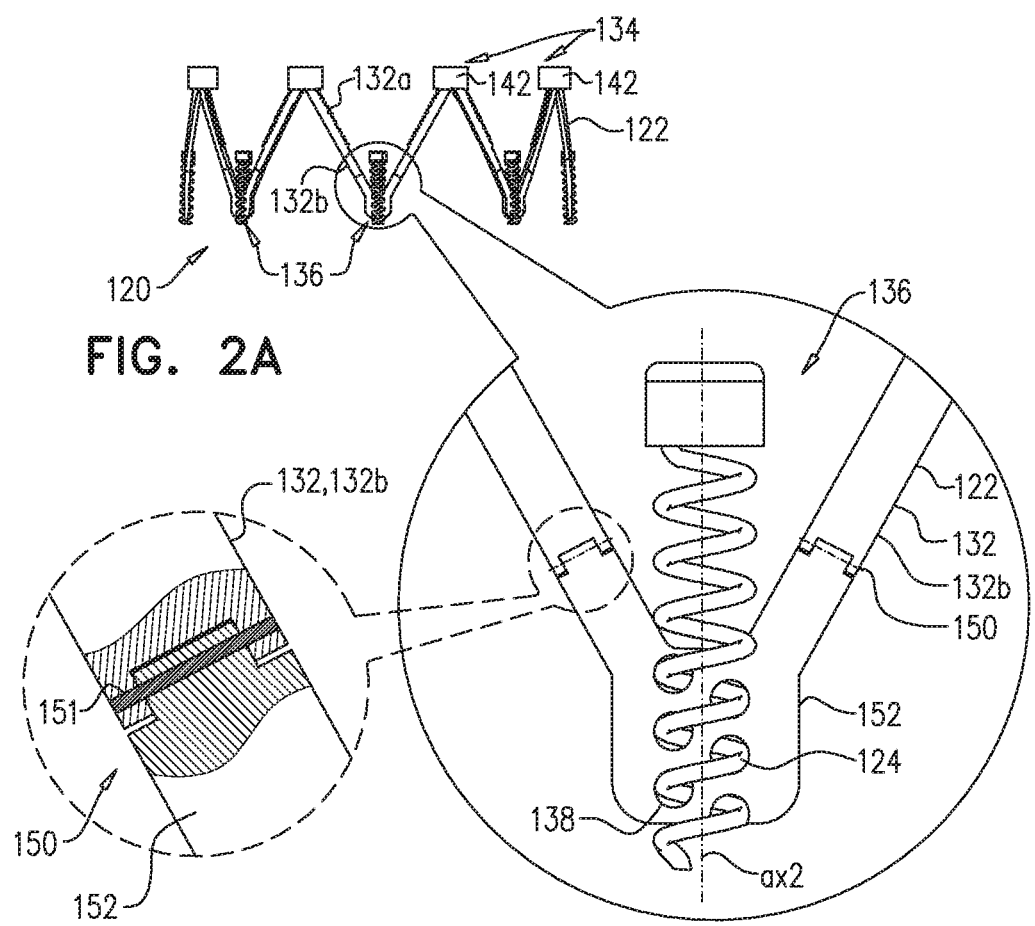
FIGS. 2A-B, 3A-B, and 4 are schematic illustrations of respective implants for use at a valve of a heart of a subject, in accordance with some applications of the invention.
Figure 2B:
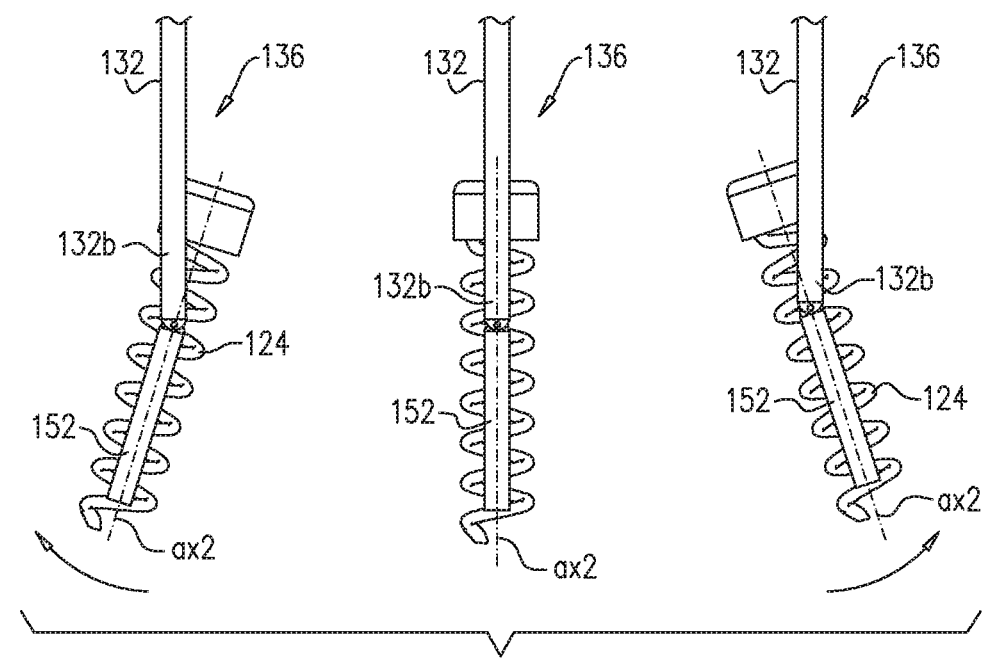
Figure 3A:
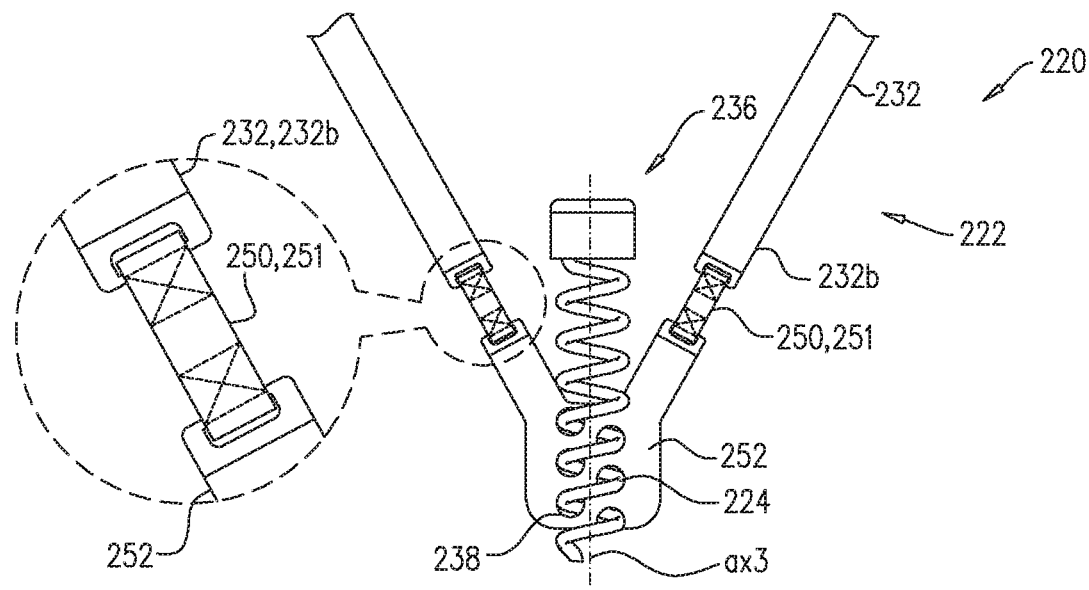
Figure 3B:
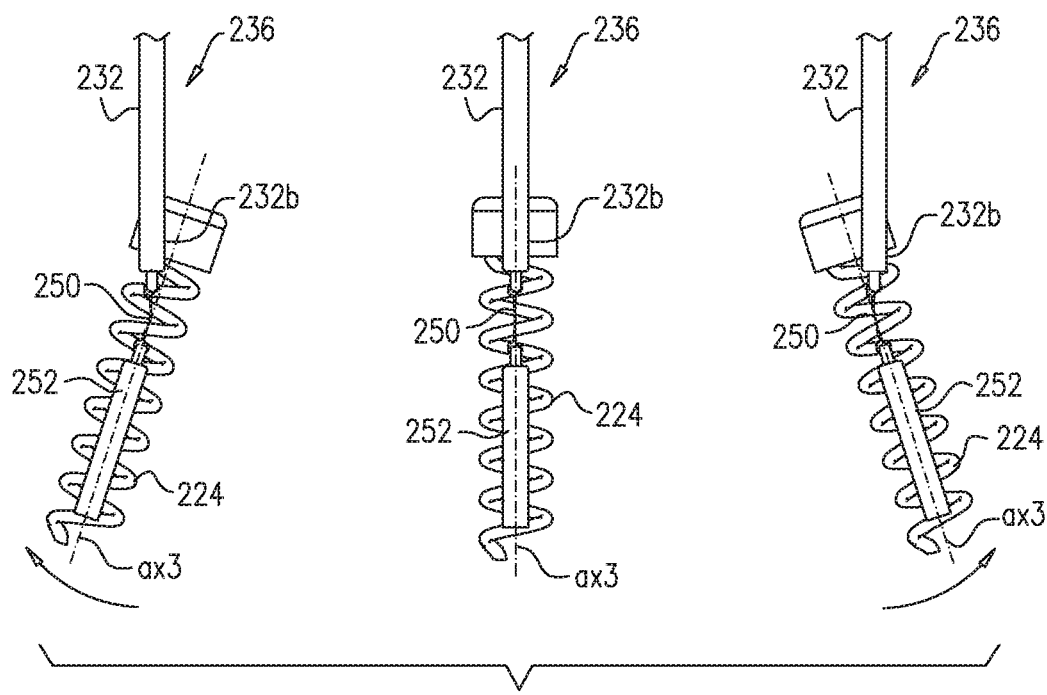
Figure 4:
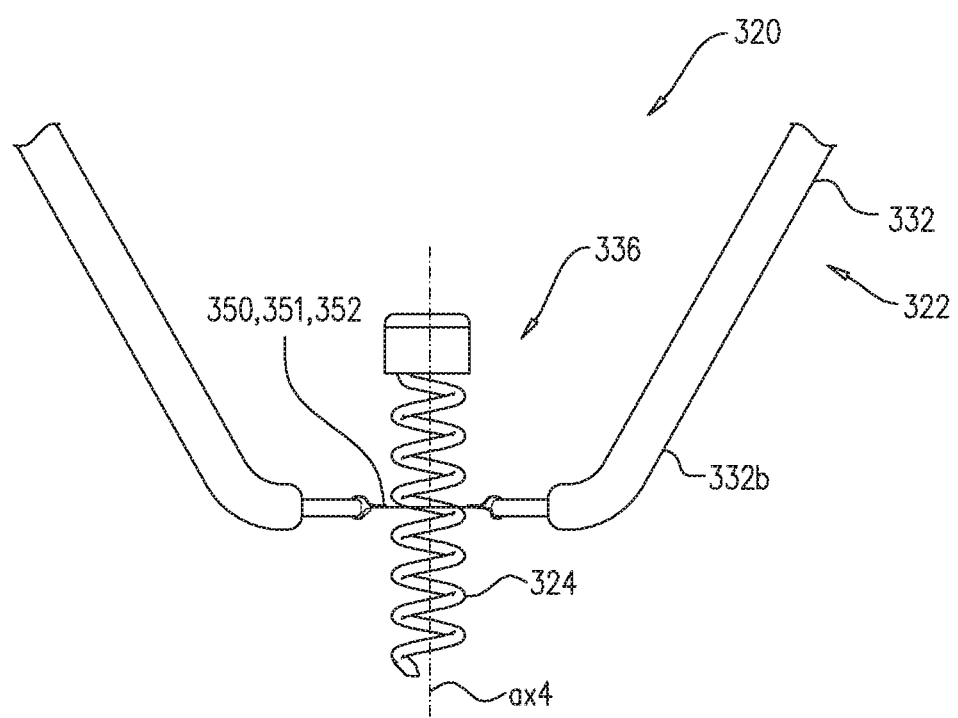

Reference is now made to FIGS. 2A-B, 3A-B, and 4, which are schematic illustrations of respective implants for use at a valve of a heart of a subject, in accordance with some applications of the invention. FIGS. 2A-B show an implant 120, FIGS. 3A-B show an implant 220, and FIG. 4 shows an implant 320. Unless noted, the structure, function, and use of implants 120, 220, and 320 are similar to those of implant 20. Unless noted, the components of implants 120, 220 and 320 generally correspond to identically-named components of implant 20, mutatis mutandis. The reference numerals assigned to the components of implants 120, 220 and 320 are intended to further illustrate this relationship.

For example, struts 132 of implant 120 generally correspond to struts 32 of implant 20, mutatis mutandis (as do struts 232 of implant 220, and struts 332 of implant 320). Implants 120, 220, and 320 are typically delivered transluminally (e.g., transfemorally).

Implant 120 (FIGS. 2A-B) comprises a ring 122 and a plurality of anchors 124. Ring 122 comprises a plurality of struts 132 arranged in a pattern of alternating peaks 134 and troughs 136 (e.g., in a zig-zag pattern). Each strut 132 has a first end-portion 132a and a second end-portion 132b. Each peak 134 is defined by convergence of adjacent first end-portions 132a (i.e., of first end-portions 132a of adjacent struts 132), and each trough 136 is defined by convergence of adjacent second end-portions 132b (i.e., of second end-portions 132b of adjacent struts 132). Similarly to implant 20, implant 120 comprises an adjustment element 142 for each pair of adjacent first-end portions 132a.

Each anchor 124 has a longitudinal axis ax2 along which it is configured to be driven into tissue of the annulus of the valve of the heart of the subject, and is coupled to ring 122 at a respective trough 136 in a manner that facilitates movement of the anchor along the longitudinal axis with respect to the trough. At each trough 136, ring 122 defines a plurality of holes 138 through which anchor 124 is moveable. Typically, each anchor 124 comprises a helical tissue-engaging element and an anchor head (e.g., as described for anchor 24) and is shaped and rotatably coupled to ring 122 at the respective trough 136 such that rotation of the anchor with respect to the ring moves the anchor along its longitudinal axis with respect to the trough (e.g., corkscrews the anchor through holes 138 such that the anchor moves longitudinally).

In contrast to anchors 24 of implant 20, anchors 124 of implant 120 are coupled to ring 122 at respective troughs 136 in a manner that facilitates both (i) movement of the anchor along axis ax2 with respect to the trough, and (ii) deflection of axis ax2 with respect to the trough. That is, as well as moving axially, each anchor 124 can deflect with respect to ring 122 (e.g., with respect to struts 132 thereof). It is hypothesized by the inventors that this facilitates anchoring of implant 120 to the annulus, e.g., by allowing independent orientation of each anchor according to the tissue to which it is to be anchored.

Typically, and as shown, implant 120 (e.g., ring 122 thereof) comprises a plurality of hinges 150, at least one of which is disposed at each trough 136, and the anchor 124 disposed at that trough is coupled to ring 122 via the hinge. Hinge 150 may be a barrel hinge (e.g., comprising a pin 151, as shown), a flexure bearing, or any other suitable hinge type. For some applications, and as shown, the at least one hinge 150 of each trough 136 couples, to each other, the adjacent second end-portions 132b that define that trough. Alternatively, the adjacent second end-portions 132b may be coupled independently of the at least one hinge 150, and the at least one hinge couples anchor 124 to the trough independently of the coupling between the adjacent second end-portions (embodiment not shown).

For some applications, and as shown, implant 120 (e.g., ring 122 thereof) comprises, at each trough 136, an anchor mount 152 that is articulatably coupled to struts 132 (e.g., to second end-portions 132b), e.g., via the at least one hinge 150. Typically, each anchor mount 152 is coupled to one second end-portion 132b via one hinge 150, and to another second end-portion 132b via another hinge. Anchor mount 152 defines the holes 138 of implant 120.

FIG. 2A shows implant 120, with a magnification of a trough 136, and a further magnification of a hinge 150. FIG. 2B illustrates the articulation, at a trough 136, between ring 122 and an anchor 124 (e.g., via the articulated coupling between an anchor mount 152 and struts 132).

Implant 220 (FIGS. 3A-B) comprises a ring 222 and a plurality of anchors 224. Similar to rings 22 and 122, ring 222 comprises a plurality of struts 232 arranged in a pattern of alternating peaks (not shown) and troughs 236 (e.g., in a zig-zag pattern). Each strut 232 has a first end-portion (not shown) and a second end-portion 232b. Each peak is defined by convergence of adjacent first end-portions (i.e., of first end-portions of adjacent struts 232), and each trough 236 is defined by convergence of adjacent second end-portions 232b (i.e., of second end-portions 232b of adjacent struts 232). Similarly to implants 20 and 120, implant 220 comprises an adjustment element (not shown) for each pair of adjacent first-end portions.

Each anchor 224 has a longitudinal axis ax3 along which it is configured to be driven into tissue of the annulus of the valve of the heart of the subject, and is coupled to ring 222 at a respective trough 236 in a manner that facilitates movement of the anchor along the longitudinal axis with respect to the trough. At each trough 236, ring 222 defines a plurality of holes 238 through which anchor 224 is moveable. Typically, each anchor 224 comprises a helical tissue-engaging element and an anchor head (e.g., as described for anchor 24) and is shaped and rotatably coupled to ring 222 at the respective trough 236 such that rotation of the anchor with respect to the ring moves the anchor along its longitudinal axis with respect to the trough (e.g., corkscrews the anchor through holes 238 such that the anchor moves longitudinally).

In contrast to anchors 24 of implant 20, and similarly to anchors 124 of implant 120, anchors 224 of implant 220 are coupled to ring 222 at respective troughs 236 in a manner that facilitates both (i) movement of the anchor along axis ax3 with respect to the trough, and (ii) deflection of axis ax3 with respect to the trough. That is, as well as moving axially, each anchor 224 can deflect with respect to ring 222 (e.g., with respect to struts 232 thereof). It is hypothesized by the inventors that this facilitates anchoring of implant 220 to the annulus, e.g., by allowing independent orientation of each anchor according to the tissue to which it is to be anchored.

Typically, and as shown, implant 220 (e.g., ring 222 thereof) comprises a plurality of hinges 250, at least one of which is disposed at each trough 236, and the anchor 224 disposed at that trough is coupled to ring 222 via the hinge. Hinge 250 comprises a flexible strip 251, such as a strip of fabric. It is to be noted that although this element is named a "strip," and is shown having a width that is greater than its thickness, and a length that is greater than its width, the term "strip" (including the specification and the claims) is not intended to limit this element to such dimensions. For some applications, and as shown, the at least one hinge 250 of each trough 236 couples, to each other, the adjacent second end-portions 232b that define that trough. Alternatively, the adjacent second end-portions 232b may be coupled independently of the at least one hinge 250, and the at least one hinge couples anchor 224 to the trough independently of the coupling between the adjacent second end-portions (embodiment not shown).

For some applications, and as shown, implant 220 (e.g., ring 222 thereof) comprises, at each trough 236, an anchor mount 252 that is articulatably coupled to struts 232 (e.g., to second end-portions 232b), e.g., via the at least one hinge 250. Typically, each anchor mount 252 is coupled to one second end-portion 232b via one hinge 250, and to another second end-portion 232b via another hinge. Anchor mount 252 defines the holes 238 of implant 220.

For some applications, hinge 250 provides a further degree of movement compared to hinge 150 of implant 120. For example, due to the flexibility of the flexible strip, anchor mount 252 may be twisted and/or deflected asymmetrically with respect to struts 232.

FIG. 3A shows a magnification of a trough 236 of implant 220 (implant 220 is not shown in its entirety), and a further magnification of a hinge 250. FIG. 3B illustrates articulation, at a trough 236, between ring 222 and an anchor 224 (e.g., via the coupling between an anchor mount 252 and struts 232).

Implant 320 (FIG. 4) comprises a ring 322 and a plurality of anchors 324. Similar to rings 22, 122, and 222, ring 322 comprises a plurality of struts 332 arranged in a pattern of alternating peaks (not shown) and troughs 336 (e.g., in a zig-zag pattern). Each strut 332 has a first end-portion (not shown) and a second end-portion 332b. Each peak is defined by convergence of adjacent first end-portions (i.e., of first end-portions of adjacent struts 332), and each trough 336 is defined by convergence of adjacent second end-portions 332b (i.e., of second end-portions 332b of adjacent struts 332). Similarly to implants 20, 120, and 220, implant 320 comprises an adjustment element (not shown) for each pair of adjacent first-end portions.

Each anchor 324 has a longitudinal axis ax4 along which it is configured to be driven into tissue of the annulus of the valve of the heart of the subject, and is coupled to ring 322 at a respective trough 336 in a manner that facilitates movement of the anchor along the longitudinal axis with respect to the trough. At each trough 336, ring 322 defines at least one hole through which anchor 324 is moveable. Typically, each anchor 324 comprises a helical tissue-engaging element and an anchor head (e.g., as described for anchor 24) and is shaped and rotatably coupled to ring 322 at the respective trough 336 such that rotation of the anchor with respect to the ring moves the anchor along its longitudinal axis with respect to the trough (e.g., corkscrews the anchor through the hole such that the anchor moves longitudinally).

In contrast to anchors 24 of implant 20, and similarly to anchors 124 of implant 120 and anchors 224 of implant 220, anchors 324 of implant 320 are coupled to ring 322 at respective troughs 336 in a manner that facilitates both (i) movement of the anchor along axis ax4 with respect to the trough, and (ii) deflection of axis ax4 with respect to the trough. That is, as well as moving axially, each anchor 324 can deflect with respect to ring 322 (e.g., with respect to struts 332 thereof). It is hypothesized by the inventors that this facilitates anchoring of implant 320 to the annulus, e.g., by allowing independent orientation of each anchor according to the tissue to which it is to be anchored.

Typically, and as shown, implant 320 (e.g., ring 322 thereof) comprises a plurality of hinges 350, each hinge disposed at a respective trough 336, and the anchor 324 disposed at that trough is coupled to ring 322 via the hinge. Hinge 350 comprises a flexible strip 351, such as a strip of fabric. For some applications, and as shown, the hinge 350 of each trough 336 couples, to each other, the adjacent second end-portions 332b that define that trough. Alternatively, the adjacent second end-portions 332b may be coupled independently of the at least one hinge 350, and the at least one hinge couples anchor 324 to the trough independently of the coupling between the adjacent second end-portions (embodiment not shown).

In contrast to implant 220, implant 320 (e.g., ring 322 thereof) typically does not comprise distinct anchor mount. Rather, anchor 324 passes directly through flexible strip 351, and the flexible strip serves as an anchor mount 352, as well as providing the articulation functionality of hinge 350. Strip 351 thereby defines the hole of each trough 336 of implant 320.

For some applications, hinge 350 provides a further degree of movement compared to hinge 150 of implant 120. For example, due to the flexibility of the flexible sheet or strip, anchor 324 may be twisted and/or deflected asymmetrically with respect to struts 332.

FIG. 3A shows a magnification of a trough 336 of implant 320 (implant 320 is not shown in its entirety). FIG. 3B illustrates articulation, at a trough 336, between ring 322 and an anchor 324.

Figure 5:
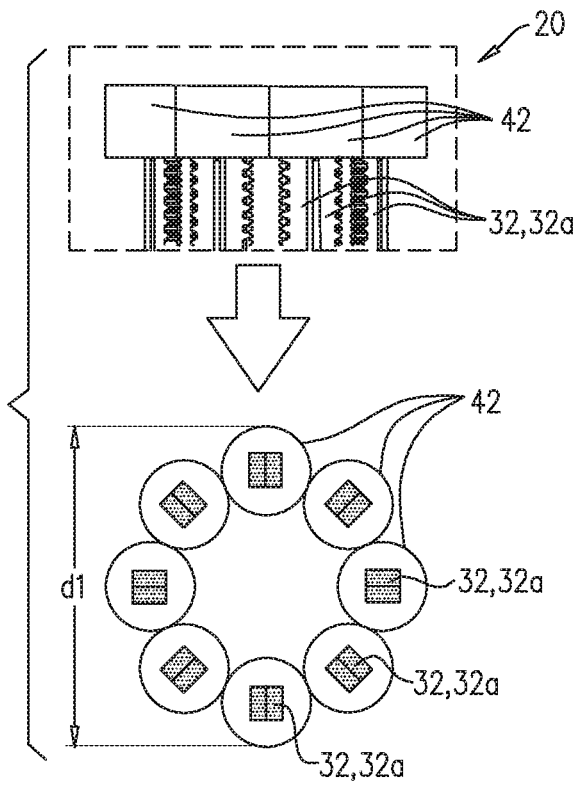
FIGS. 5 and 6A-B are schematic illustrations of compressed states of implants, in accordance with some applications of the invention.
Figure 6A:
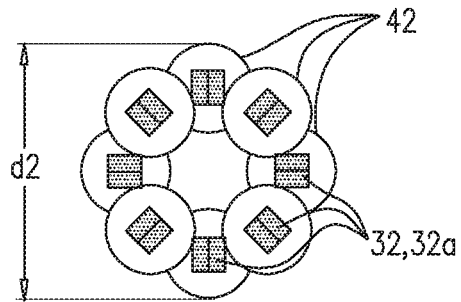
Figure 6B:
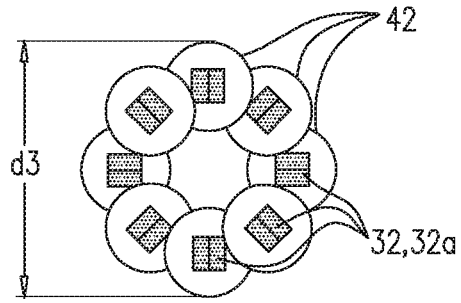

Reference is made to FIGS. 5, and 6A-B, which are schematic illustrations of compressed states of implants, in accordance with some applications of the invention. Implant 20 is used as an example, but the compressed states may apply to the other implants described herein. FIG. 5 shows a partial side view and a top view of implant 20 in its compressed state, e.g., as it would be while disposed within catheter 40, e.g., as shown in FIG. 1A. (The partial side view is taken from U.S. Pat. No. 9,180,005, whereas the top view is based on the inventors' understanding of that reference.) Adjustment elements 42 are disposed at the same longitudinal position on the implant as each other, and because theyABE wider than the strut-pairs to which they are coupled, they abut each other, and effectively define the widest part of implant 20 in its compressed state. The diameter of implant 20 at this widest part is shown as d1.

FIGS. 6A and 6B show alternative arrangements of adjustment elements 42 in alternative compressed states of implant 20. FIG. 6A shows adjustment elements 42 arranged in an alternating up-down pattern, and FIG. 6B shows the adjustment elements arranged in two sets of four steps. Both of these arrangements allow better compression of implant 20, such that the implant has a diameter d2 or d3 that is smaller than diameter d1. It is to be noted that diameters d2 and d3 are typically smaller than the diameter of a circle formed when all the adjustment elements 42 are arranged in a circle, touching each other.

Figure 7:
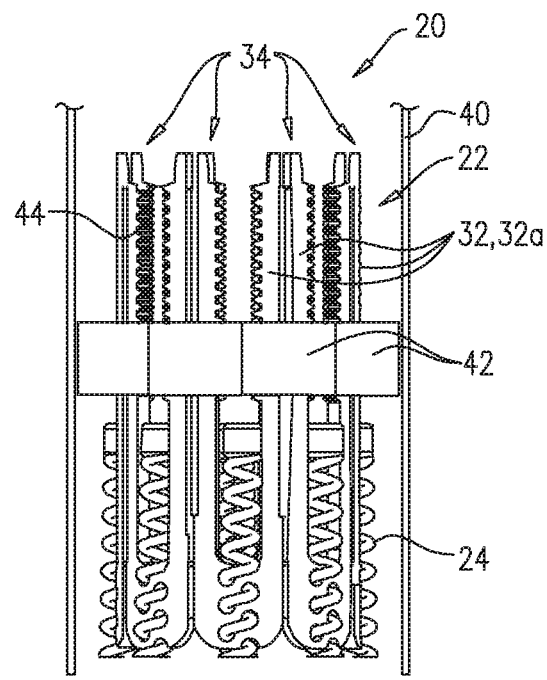
FIG. 7 is a schematic illustration of an implant in its compressed state, in accordance with some applications of the invention.

Reference is made to FIG. 7, which is a schematic illustration of an implant in its compressed state, in accordance with some applications of the invention. Implant 20 is used as an example, but the compressed state may apply to the other implants described herein. As described hereinabove, in a prior art technique, when implant 20 is deployed from catheter 40, it automatically expands into an expanded state. For such a technique, adjustment elements 42 are positioned such that they allow maximal or near-maximal expansion of ring 22 upon deployment of implant 20—e.g., at or close to peaks 34, and/or at or close to an upstream end of threads 44. In the technique of FIG. 7, adjustment elements 42 are positioned such that the restrict expansion of ring 22 upon deployment of implant 20—e.g., closer toward (e.g., at or close to) the downstream end of threads 44. Thus, upon deployment of implant 20 from catheter 40, the implant doesn't automatically expand (or at least not fully). The operator may then expand implant 20 in a controlled and/or stepwise manner by actuating adjusting elements 42 (e.g., such that they move toward peaks 34).

Figure 8:
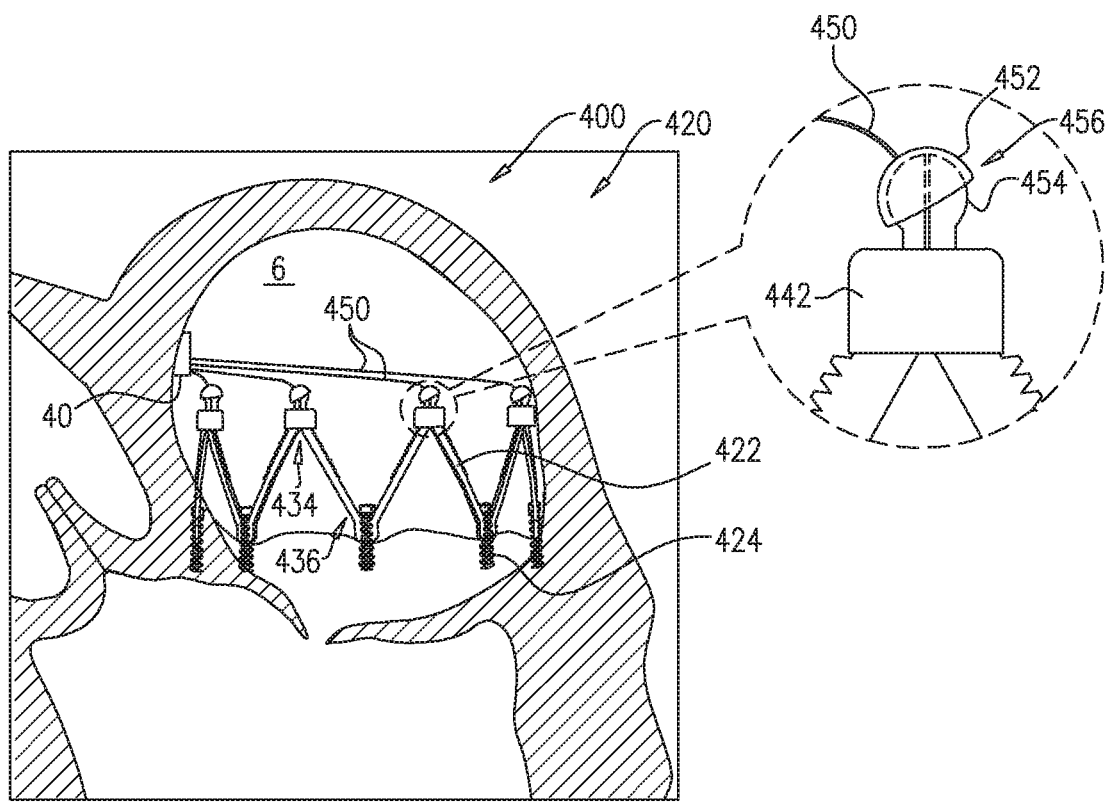
FIG. 8 is a schematic illustration of a system that comprises an implant, in accordance with some applications of the invention.

Reference is made to FIG. 8, which is a schematic illustration of a system 400, which comprises an implant 420, in accordance with some applications of the invention. Implant 420 comprises a ring 422 and a plurality of anchors 424. Ring 422 comprises a plurality of struts arranged in a pattern of alternating peaks 434 and troughs 436, e.g., as described herein for other implants. Similarly to other implants described herein, implant 420 comprises an adjustment element 442 for each pair of adjacent struts, e.g., disposed close to (e.g., at) each peak 434. In order to actuate (e.g., rotate) adjustment element 442, an adjustment tool is typically advanced through catheter 40 to the adjustment element. To facilitate guidance of the adjustment tool to the adjustment element, system 400 comprises a plurality of elongate guide members 450 (e.g., one for each adjustment element 442), coupled to ring 422 close to (e.g., at) each peak 434, and extending proximally into catheter 40. The adjustment tool is advanced along the elongate guide member 450 to the adjustment element 442.

Implant 420 (and the other implants described herein, including implant 20) are typically taller than annuloplasty rings known in the art, and therefore peaks 434 and adjustment elements 442 are relatively high within atrium 6. For example, peaks 434 may be only a little inferior to, at the same height as, or even superior to the site at which catheter 40 enters atrium 6 (e.g., the fossa ovalis). Each guide member 450 is coupled to ring 422 (e.g., at a respective peak 434) via a bearing 456. For example, and as shown, bearing 456 may be a ball-and-socket bearing comprising a ball 454 (e.g., defined by implant 420) and a socket 452 (e.g., coupled to, or defined by, a distal end of the guide member 450). Bearing 456 facilitates articulation between the distal end of guide member 450 and implant 420, thereby allowing adjustment elements 442 to be positioned high within atrium 6, while coupled to the guide members.

Reference is made to FIGS. 9A-J, which are schematic illustrations of a system 500, which comprises a plurality of subunits 502 that are intracorporeally assembled to form an implant 520, in accordance with some applications of the invention. Once assembled, implant 520 is similar to implant 20 and/or to another of the implants described herein, mutatis mutandis. System 500 facilitates transfemoral delivery of such an implant, by providing the implant as subunits 502, which individually have a smaller profile than that of a similar implant that is delivered pre-assembled. Thus system 500 may be considered to be a modification of any of the implants described herein, and FIGS. 9A-J may be considered to illustrate a technique for delivering such a modified implant.

Each subunit 502 comprises a pair of struts that comprises a first strut 532 (which has a first end-portion 532a and a second end-portion 532b) and a second strut 533 (which has a first end-portion 533a and a second end-portion 533b). Each subunit defines a trough 536 at which the second end-portion of each strut of the pair is coupled to the second end-portion of the other strut of the pair (i.e., end-portion 532b is coupled to end-portion 533b).

A first subunit 502a is transfemorally delivered to the native heart valve (e.g., in a compressed state, within a catheter 540), typically into an atrium such as the left atrium 6 of the heart (FIG. 9A). Subsequently, the trough 536 of subunit 502a is anchored to tissue 10 that surrounds the valve (e.g., tissue of the valve annulus) by driving a tissue anchor 524 into the tissue, such as by using an anchor driver tool 504, which may be used to facilitate deployment of the subunit out of catheter 540 (FIGS. 9B-C).

Subsequently, first end-portion 533a of second strut 533 of subunit 502a is secured to first end-portion 532a of first strut 532 of another subunit 502b, such that the secured first end-portions converge at an angle alpha_1 to define a peak 534 (FIGS. 9D-G). For example, and as shown, end-portion 533a of first subunit 502a may have an elongate guide member 506 attached thereto, the guide member extending proximally from end-portion 533a of the implanted subunit (e.g., into a delivery sheath, such as to outside of the subject), and end-portion 532a of subunit 502b is advanced over and along the guide member, guided by the guide member to end-portion 533a of subunit 502a. Subunit 502b is anchored to tissue 10 in the same way as subunit 502a.

Typically, an adjustment element 542 is subsequently coupled to the first end-portions that define each peak (FIG. 9G). For some applications, this further secures these two end-portions to each other. For example, for applications in which adjustment element 542 comprises a nut (e.g., as described hereinabove, mutatis mutandis), the nut is typically screwed onto the threads defined by the end-portions (e.g., using a tool 508 that is reversibly coupled to the adjustment element, and is slidable over and along guide member 506), thereby securing the end-portions to each other.

Subsequently to the steps of anchoring and securing, the angle alpha_1 defined by each peak 534 is reduced by actuating the adjustment element 542 of that peak, e.g., using tool 508. This reduces a distance d4 between anchors 524 of the adjacent subunits, thereby reducing the circumference of a portion of the annulus of the valve being treated. The adjustment is shown in FIG. 9H in order to illustrate that the adjustment of each adjustment element 542 may be performed after each subunit 502 is secured. Alternatively, the adjustment may be deferred until after more than one (e.g., all) of the subunits have been secured (e.g., similarly to implant 20).

Figure 9J:
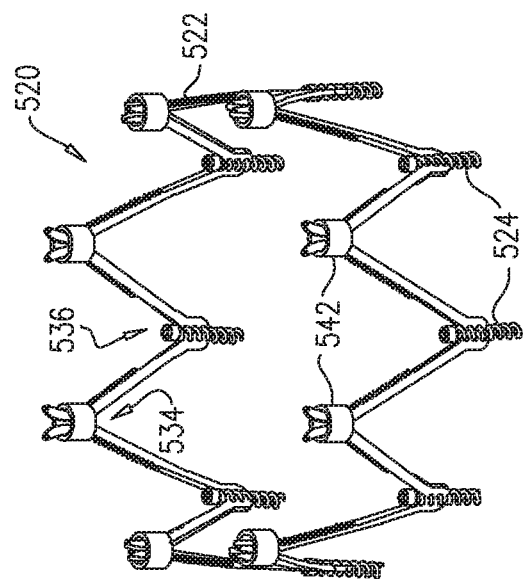
Figure 9I:
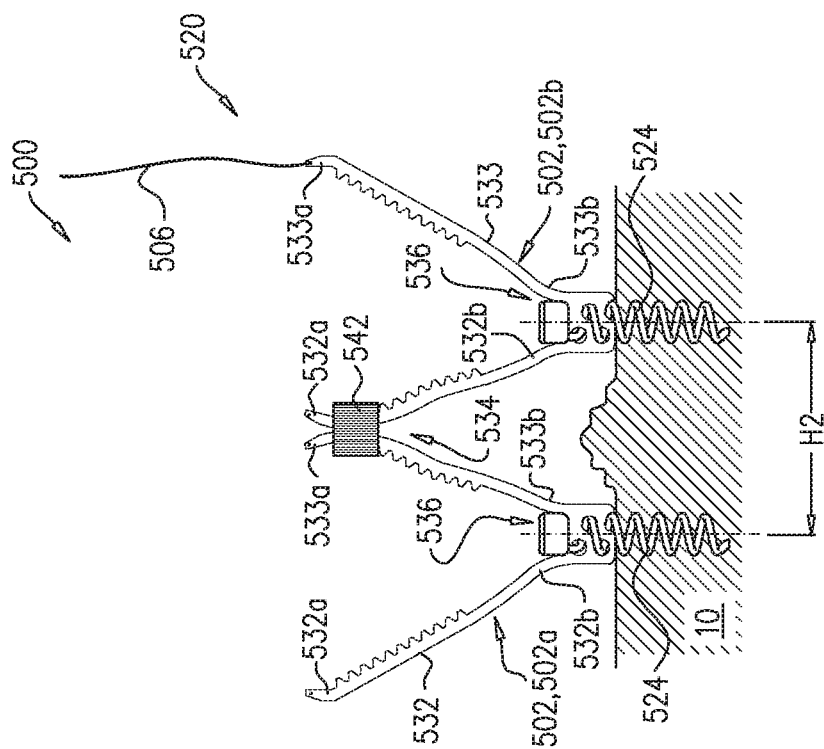

Following implantation, guide member 506 is typically decoupled from implant 520 and removed from the subject (FIG. 9I). This may be achieved by unthreading and/or cutting each guide member 506 (e.g., facilitated by tool 508), or by any other suitable technique known in the art.

The above process is repeated iteratively, mutatis mutandis, until implant 520 has been fully assembled, e.g., formed into a full ring such as that of implant 20, or into a partial ring or band (FIG. 9J).

The techniques described with reference to FIGS. 9A-J may be used to assemble implants similar to implants 20, 120, 220 and 320, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
advancing, to a valve of a heart of a subject, an implant that includes:
a main body, including (i) a plurality of struts, and (ii) a hinge, the main body circumscribing a central axis, and wherein the hinge is disposed at a trough between a first pair of adjacent struts of the plurality of struts,
an anchor coupled to the main body at the hinge,
a peak defined by convergence of a second pair of adjacent struts of the plurality of struts, the second pair of adjacent struts being disposed at a strut angle with respect to each other, and an adjustment element, rotatably coupled to the peak such that rotation of the adjustment element with respect to the peak changes the strut angle; and within the heart, deflecting the hinge to change a hinge angle of a portion of the hinge in a radial direction with respect to the central axis.

2. The method according to claim 1, further comprising driving the anchor along an axis that is coaxial to the hinge angle and into tissue of the heart.

3. The method according to claim 2, further comprising, subsequently to driving the anchor, contracting tissue of the heart by changing the strut angle by rotating adjustment element while the anchor remains in the tissue of the heart.

4. A method, comprising:
advancing, to a valve of a heart of a subject, an implant that includes:
a main body, including (i) a plurality of struts, and (ii) a plurality of hinges, the main body circumscribing a central axis,
a hinge of the plurality of hinges being disposed at a trough between a first pair of adjacent struts of the plurality of struts,
a peak defined by convergence of a second pair of adjacent struts of the plurality of struts, the second pair of adjacent struts being disposed at a strut angle with respect to each other, and
an adjustment element rotatably coupled to the peak such that rotation of the adjustment element with respect to peak changes the strut angle; and
within the heart, deflecting the hinge to change a hinge angle of a portion of the hinge in a radial direction with respect to the central axis.

5. The method according to claim 4, wherein the implant further includes an anchor coupled to the main body at the hinge, and wherein the method further comprises driving the anchor into tissue of the heart along an axis that is coaxial with the hinge angle.

6. The method according to claim 5, further comprising, subsequently to driving the anchor, contracting tissue of the heart by changing the strut angle by rotating the adjustment element while the anchor remains in the tissue of the heart.

7. The method according to claim 6, wherein the adjustment element circumscribes, at the peak, adjacent first end portions of the second pair of adjacent struts, and wherein rotating the adjustment element comprises rotating the adjustment element around both of the adjacent first end portions.

8. The method according to claim 7, wherein rotating the adjustment element around both of the adjacent first end portions comprises screwing the adjustment element over and along both of the adjacent first end-portions.

9. The method according to claim 4, wherein the valve of the heart is a mitral valve of the heart, and wherein advancing the implant comprises transfemorally advancing the implant into a left atrium of the heart and to the mitral valve.

10. The method according to claim 4, wherein the hinge is a flexure bearing, and wherein deflecting the hinge to change the hinge angle comprises flexing the flexure bearing.

11. The method according to claim 4, wherein:
the implant is a zig-zag shaped implant, the zig-zag shape of the implant defined by a pattern of peaks and troughs of the plurality of struts, wherein the peak is one of the peaks and the trough is one of the troughs, and
advancing the implant comprises advancing the zig-zag shaped implant.

12. The method according to claim 4, wherein:
advancing the implant comprises advancing the implant while the implant is in a compressed state,
the method further comprises:
expanding the implant to an expanded state in which the implant has a circumference that is greater than in the compressed state,
anchoring the implant to tissue of the valve of the heart, and
while the implant remains anchored to the tissue, contracting the tissue by contracting the implant toward its compressed state,
wherein contracting the implant toward its compressed state comprises changing the strut angle by rotating the adjustment element.

13. The method according to claim 12, wherein:
expanding the implant to the expanded state comprises rotating the adjustment element in a first rotational direction, and
contracting the tissue by rotating the at least one adjustment element comprises, while the implant remains anchored to the tissue, contracting the tissue by contracting the implant toward its compressed state,
wherein contracting the implant toward its compressed state comprises changing the strut angle by rotating the adjustment element in a second rotational direction that is opposite to the first rotational direction.

* * * * *